United States Patent [19]
Brenner et al.

[11] 3,947,470
[45] Mar. 30, 1976

[54] SUBSTITUTED BENZOFURANS AND BENZOTHIOPHENES

[75] Inventors: L. Martin Brenner, Havertown, Pa.; John M. Petta, Willingboro, N.J.; Stephen T. Ross, Berwyn, Pa.

[73] Assignee: SmithKline Corporation, Philadelphia, Pa.

[22] Filed: June 20, 1974

[21] Appl. No.: 481,283

[52] U.S. Cl. .......... 260/330.5; 260/343.7; 260/253; 424/275; 424/285; 260/346.2 R
[51] Int. Cl.² ...................................... C07D 333/56
[58] Field of Search............. 260/330.5, 346.2, 253, 260/343.7

[56] References Cited
UNITED STATES PATENTS

| | | | |
|---|---|---|---|
| 3,248,401 | 4/1966 | Tondeur et al. | 260/346.2 |
| 3,658,845 | 4/1972 | Posselt et al. | 260/330.5 |
| 3,706,747 | 12/1972 | DeAngelis et al. | 260/265.5 A |
| 3,880,891 | 4/1975 | Hill et al. | 260/346.2 R |

FOREIGN PATENTS OR APPLICATIONS

| | | | |
|---|---|---|---|
| 2,130,480 | 3/1972 | Germany | 260/346.2 |
| 2,230,669 | 12/1972 | Germany | 260/330.5 |
| 1,080,114 | 4/1960 | Germany | 260/346.2 |
| 1,079,066 | 4/1960 | Germany | 260/346.2 |

OTHER PUBLICATIONS

Charlier et al., C. A. Vol. 80:43994w.

*Primary Examiner*—John D. Randolph
*Assistant Examiner*—C. M. S. Jaisle
*Attorney, Agent, or Firm*—Janice E. Williams; Alan D. Lourie; William H. Edgerton

[57] ABSTRACT

The compounds of this invention are substituted benzofurans and benzothiophenes having pharmacological activity. In particular, these compounds have coronary vasodilator activity and are useful in the treatment angina pectoris.

12 Claims, No Drawings

SUBSTITUTED BENZOFURANS AND BENZOTHIOPHENES

This invention relates to new substituted benzofurans and benzothiophenes which have useful pharmacological activity. More specifically, the compounds of this invention have coronary vasodilator activity and are useful in the treatment of angina pectoris. In addition, these compounds may be useful as hypotensive agents.

The compounds of this invention are represented by the following structural formula:

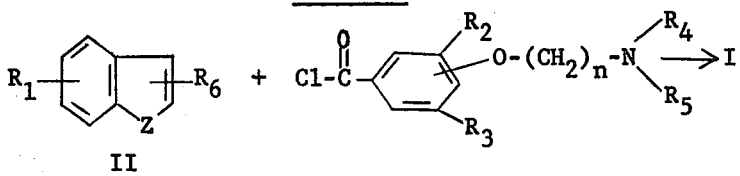

or a pharmaceutically acceptable acid addition salt thereof, in which:

$R_1$ is hydrogen, halo, trifluoromethyl, nitro, lower alkyl or lower alkoxy;

$R_2$ and $R_3$ are hydrogen, lower alkyl or lower alkoxy;

$R_4$ is hydrogen or straight chain lower alkyl;

$R_5$ is straight chain lower alkyl;

$R_6$ is phenyl, lower alkylphenyl, di-lower alkylphenyl, tri-lower alkylphenyl, lower alkoxyphenyl, di-lower alkoxyphenyl, tri-lower alkoxyphenyl, halophenyl, dihalophenyl, trihalophenyl, trifluoromethylphenyl, benzyl, halobenzyl, lower alkylbenzyl, lower alkoxybenzyl or trifluoromethylbenzyl;

$n$ is 2 to 4; and

Z is oxygen or sulfur.

As used herein, the terms "lower alkyl" and "lower alkoxy" denote groups having from one to four carbon atoms; "halo" refers to chloro, bromo and fluoro.

Advantageous compounds of this invention are represented by formula I in which the aminoalkoxy side chain is in the para position on the benzoyl ring; $R_1$ is hydrogen or halo in the 5-position; $R_2$ and $R_3$ are hydrogen; $R_4$ and $R_5$ are ethyl, n-propyl or n-butyl; and $R_6$ is phenyl, tolyl, chlorophenyl, bromophenyl, methoxyphenyl, trifluoromethylphenyl, dimethylphenyl, dichlorophenyl, dimethoxyphenyl, trimethoxyphenyl, chlorobenzyl or trifluoromethylbenzyl.

Preferred compounds of this invention are represented by formula I in which the aminoalkoxy side chain is in the para position on the benzoyl ring; $R_1$ is hydrogen or chloro in the 5-position; $R_2$ and $R_3$ are hydrogen; $R_4$ and $R_5$ are ethyl, n-propyl or n-butyl; $R_6$ is phenyl, p-tolyl, p-chlorophenyl, p-methoxyphenyl, 3,5-dimethylphenyl, 3,4-dichlorophenyl, 3,4-dimethoxyphenyl, 3,4,5-trimethoxyphenyl, p-chlorobenzyl or m-trifluoromethylbenzyl; and $n$ is 3.

Particularly preferred are the compounds 3-[4-(3-diethylaminopropoxy)benzoyl]-2-phenylbenzofuran, 3-[4-(3-di-n-propylaminopropoxy)benzoyl]-2-phenylbenzofuran, 3-[4-(3-diethylaminopropoxy)benzoyl]-2-(4-tolyl)benzofuran, 3-[4-(3-diethylaminopropoxy)benzoyl]-2-(4-methoxyphenyl)benzofuran, 5-chloro-3-[4-(3-diethylaminopropoxy)benzoyl]-2-phenylbenzofuran, 2-[4-(3-diethylaminopropoxy)benzoyl]-3-phenylbenzofuran, 3-(4-chlorophenyl)-2-[4-(3-diethylaminopropoxy)benzoyl]benzofuran and 3-[4-(3-diethylaminopropoxy)benzoyl]-2-phenylbenzothiophene.

The compounds of formula I are prepared as shown in the following scheme:

SCHEME A

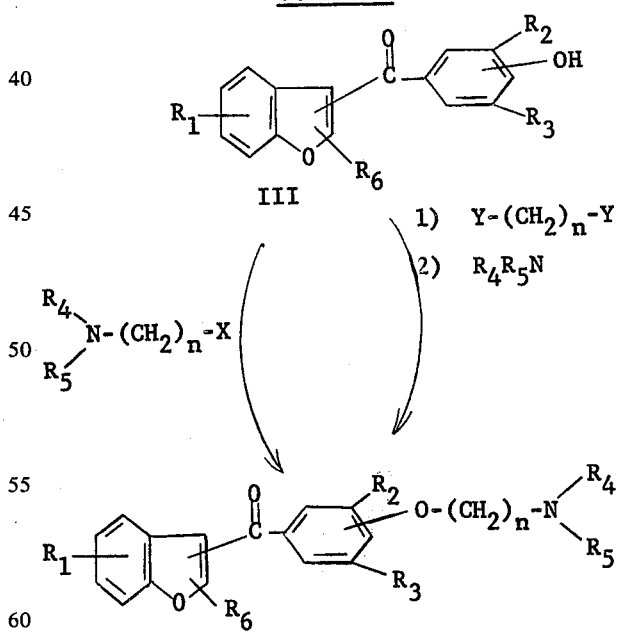

where $R_1$, $R_2$, $R_3$, $R_4$, $R_5$, $R_6$, $n$ and Z are defined as above.

Thus, a benzofuran or benzothiophene nucleus is acylated with a substituted-aminoalkoxybenzoyl chloride or its corresponding salt, preferably hydrochloride salt, by standard procedures, for example in the presence of stannic chloride or aluminum chloride in a solvent such as methylene chloride, nitrobenzene or carbon disulfide at a temperature from about 0°C. to ambient temperature (ca. 25°C.). This method of preparing the compounds of formula I is particularly advantageous when Z is sulfur or when one or more of $R_1$, $R_2$ and $R_3$ are lower alkoxy and/or $R_6$ contains an alkoxy group(s).

When Z is oxygen, the benzofuran compounds of formula I are also prepared as shown in Scheme B:

SCHEME B in which the terms $R_1$, $R_2$, $R_3$, $R_4$, $R_5$, $R_6$ and $n$ are defined as above; X is halo, preferably chloro, or a leaving group such as tosyl or mesyl; and Y is halo, preferably chloro or bromo.

According to the above procedure, reaction of a hydroxyphenyl benzofuranyl ketone of formula III with a substituted-aminoalkyl halide, tosylate or mesylate of the formula $R_4R_5N-(CH_2)_n-X$ in the presence of a base such as potassium carbonate, sodium methoxide or sodium hydride in a solvent such as acetone, methanol, ethanol, toluene, 2-butanone, 3-pentanone or dimethylsulfoxide at a temperature of about 25°C. to the reflux temperature of the solvent for from about 6 to about 24 hours gives compounds of formula I where Z is oxygen.

The benzofuran compounds of formula I are also prepared as shown in Scheme B by reaction of a hydroxyphenyl benzofuranyl ketone (III) with a dihaloalkane, Y—(CH$_2$)$_n$—Y, preferably dibromo or dichloro, in the presence of a base such as potassium carbonate in a solvent such as acetone or 3-pentanone, preferably at the reflux temperature of the solvent followed by treatment of the product haloalkoxybenzoyl benzofuran with an amine of the formula R$_4$R$_5$NH.

The products of formula I are isolated and purified as such by standard techniques including solvent extraction, crystallization and chromatographic methods or as the corresponding acid addition salts which are also objects of this invention. The salts are formed with organic and inorganic acids according to methods known to the art. Thus, a solution of the amine in ether, chloroform or an alcohol such as methanol or ethanol is treated with a solution of an organic or inorganic acid in an aqueous miscible solvent, such as acetone or ethanol, with isolation of the salt by concentration and cooling or in an aqueous immiscible solvent, such as ether, with the desired salt separating directly. Exemplary of such organic salts are those with maleic, fumaric, benzoic, ascorbic, pamoic, succinic, hexamic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well known to the art. The salts may be purified by the standard methods described above.

The hydroxyphenyl benzofuranyl ketone starting materials of Scheme B are either known to the art or are prepared as outlined below:

SCHEME C

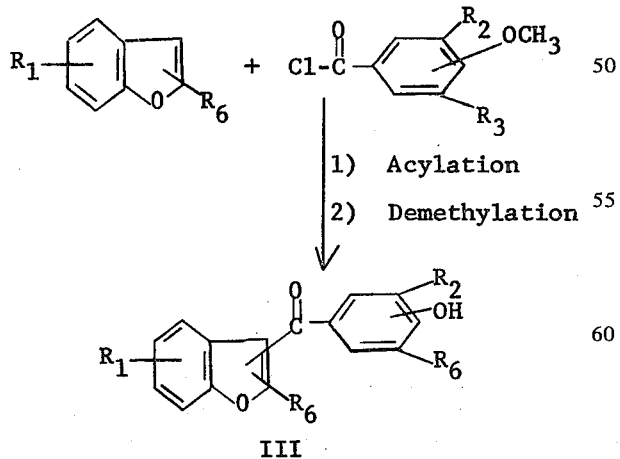

where R$_1$, R$_2$, R$_3$ and R$_6$ are defined as above.

According to Scheme C, a methoxybenzoyl chloride is used to acylate a benzofuran nucleus by standard procedures, for example in the presence of stannic chloride or aluminum chloride in a solvent such as methylene chloride, nitrobenzene or carbon disulfide.

The methoxyphenyl benzofuranyl ketones are demethylated by known methods, for example by use of pyridine hydrochloride or boron tribromide. These and other methods are described by Buu-Hoi et al., *J. Chem. Soc.* 3693 (1955), 625 (1957), 2593 (1957), 173 (1964) and in Japanese Pat. No. 2482/64.

Alternatively, the hydroxyphenyl benzofuranyl ketone starting materials having R$_6$ in the 2-position of the benzofuran nucleus are prepared by addition of a methoxyphenyl magnesium halide to a 3-cyanobenzofuran followed by hydrolysis and subsequent demethylation as previously described.

The benzofuran starting materials in Schemes A and C are either known to the art or are prepared by one of the general methods for the synthesis of benzofurans described by Buu-Hoi et al., *J. Chem. Soc.* 3693 (1955), 625 (1957), 2593 (1957) and 173 (1964); Tanaka, *J. Amer. Chem. Soc.* 73:872 (1951); Bisagni et al., *J. Chem. Soc.* 3688 (1955); Grinev et al., *Zhur. Obshchei Khim.* 27:1087 (1957); Castro et al., *J. Org. Chem.* 28:3313 (1963), 31:4071 (1966); Rodd, *Chemistry of Carbon Compounds* Vol. IV-A, 168–191; Mustafa, *The Chemistry of Heterocyclic Compounds* Vol. 29, *Benzofurans* and French Pat. No. 1,537,206. Representative methods for preparing these starting materials are exemplified hereinafter.

The benzothiophene starting materials of Scheme A are known to the art or are prepared using a thiosalicylic acid and an α-bromophenyl or α-bromobenzyl acetic acid as starting materials according to the procedure described by Kucharczyk and Horak, *Collect. Czech. Chem. Commun.* 33:92 (1968).

The hydroxyphenyl benzofuranyl ketone starting-materials of Scheme B in which R$_6$ is in the 3-position of the benzofuran nucleus are also prepared as follows:

SCHEME D

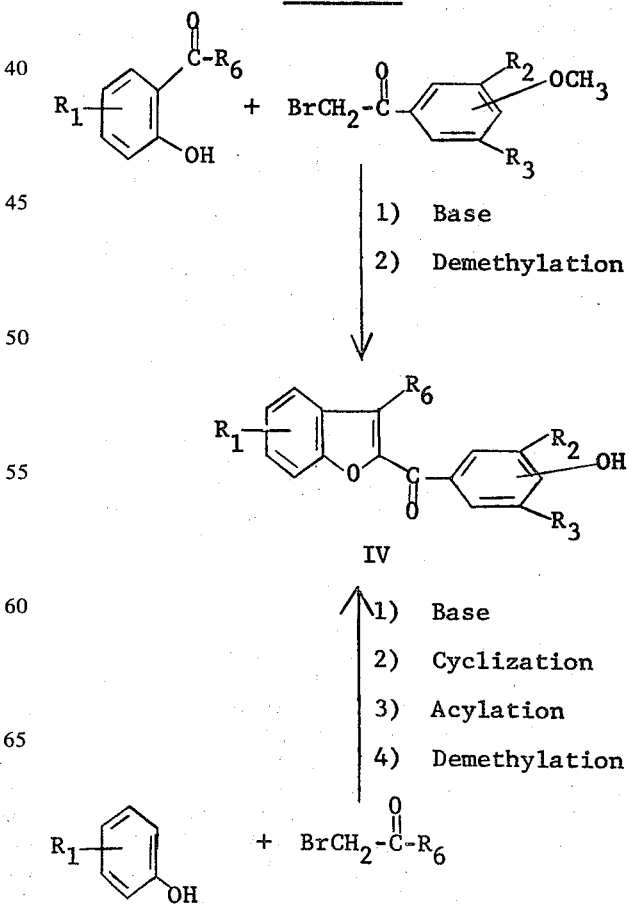

where $R_1$, $R_2$, $R_3$ and $R_6$ are defined as above.

Reaction of an o-hydroxyphenyl ketone with a substituted α-bromoacetophenone in the presence of a base, for example potassium carbonate, followed by demethylation as described above gives the hydroxyphenyl benzofuranyl ketones of formula IV.

In addition, the compounds of formula IV are prepared as shown above by reaction of a substituted phenol with an α-bromoacetophenone of the formula

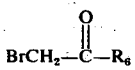

in the presence of a base such as potassium carbonate in a solvent such as acetone followed by cyclization of the intermediate thus formed, for example with polyphosphoric acid, and subsequent acylation and demethylation of the resulting 3-substituted benzofuran as described hereinabove.

The acid chloride acylating agents are either known to the art or are prepared by standard methods, for example by treatment of the corresponding acids with thionyl chloride or phosphorus pentachloride.

The coronary vasodilator activity and hypotensive effects of the compounds represented by formula I are demonstrated in dogs by an increase in coronary blood flow with concomitant decrease of mean arterial blood pressure upon intravenous administration of doses of from about 0.32 mg./kg. to about 2.5 mg./kg. These parameters are measured as follows:

Adult mongrel dogs (13–16 kg.) are pretreated with 2 mg./kg. s.c. of morphine sulfate followed in 1 hour by intravenous administration of 1–1.5 ml./kg. of an aqueous solution containing 1.5% chloralose and 20% urethane. Supplemental doses of morphine and chloralose-urethane are given to maintain an adequate and uniform depth of anesthesia.

A carotid artery is catheterized and connected to a Sanborn pressure transducer to measure arterial blood pressure. A femoral vein is also catheterized for administering a solution of the test compound or its salt and supplemental anesthesia. A left thoractomy is made at the fourth or fifth intercostal space, the lung is displaced, the pericardium is opened and the left circumflex coronary artery is isolated for measurement of coronary blood flow, a "snare" being placed around the artery distally to obtain zero flow. Coronary blood flow is measured with a Statham electromagnetic flowmeter and Flo-Probe (MDS).

In addition, the particularly preferred compounds of formula I also inhibit or attenuate the chronotropic effect of isoproterenol-induced tachycardia upon administration to dogs at doses of from about 5 mg./kg. to about 10 mg./kg. i.v. Abad et al. [*Acta Pharmacol. et Toxicol.* 25:85 (1967)] have correlated the inhibition of isoproterenol-induced tachycardia to utility as an anti-anginal agent.

Pharmaceutical compositions having coronary vasodilator activity comprising a pharmaceutical carrier and a compound of formula I and methods of producing coronary vasodilation by administering these compounds are also objects of this invention.

The pharmacologically active compounds of this invention may be administered orally or parenterally in an amount to produce the desired activity.

Preferably the compounds are administered in conventional dosage unit forms prepared by combining an appropriate dose of the compound with standard pharmaceutical carriers. The dosage units will contain the active ingredient in an amount of from about 100 mg. to about 600 mg., preferably 150 mg. to 300 mg. per dosage unit.

The pharmaceutical carrier employed may be, for example, either a solid or liquid. Exemplary of solid carriers are lactose, terra alba, sucrose, talc, gelatin, agar, pectin, acacia, magnesium, stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, solt gelatin capsule, sterile injectable liquid such as an ampule or an aqueous or nonaqueous liquid suspension.

The pharmaceutical compositions are prepared by conventional techniques involving procedures such as mixing, granulating and compressing when necessary or variously mixing and dissolving the ingredients as appropriate to the desired composition.

The method of producing coronary vasodilator activity in accordance with this invention comprises administering internally to an animal an effective amount of a compound of formula I. The compound will preferably be administered in a dosage unit form as described above orally or parenterally, the oral route being preferred. Advantageously equal doses will be administered one to two times daily with the daily dosage regimen being from about 200 mg. to about 1200 mg., preferably from about 300 mg. to about 600 mg. When the method described above is carried out, coronary vasodilator activity is produced.

One skilled in the art will recognize that in determining the amounts of the compound needed to produce the desired pharmacological effect without toxic side effects, the activity of the compound as well as the size of the host animal must be considered.

The following examples illustrate the invention but are not to be construed as limiting the scope thereof. Temperatures are in degrees Centigrade unless otherwise stated.

When formed, acid addition salts may be converted to the corresponding free amines by treating a solution of the salt in a solvent such as water, a chloroform-water or a benzene-water mixture with a base such as 10% aqueous sodium hydroxide, sodium carbonate or sodium bicarbonate until basic followed by extraction of the amine into benzene or chloroform. Salts other than hydrochlorides may be converted to the corresponding hydrochloric acid salts by passing a solution of the salt in methanol or ethanol through a chloride ion exchange column.

EXAMPLE 1

3-[4-(3-Diethylaminopropoxy)benzoyl]-2-phenylbenzofuran

To a cooled (ice bath) mixture of 7.81 g. (0.040 mol.) of 2-phenylbenzofuran and 7.0 g. (0.041 mol.) of p-anisoyl chloride in 100 ml. of methylene chloride is added dropwise 28.7 g. (0.11 mol.) of stannic chloride. The reaction mixture is allowed to warm to ambient temperature, then stirred for 2 hours. Water is slowly added to the mixture and it is stirred an additional 30 minutes. The layers are separated and the organic phase is washed with water until the washings are neutral, dried ($MgSO_4$) and concentrated to give 3-(4-methoxybenzoyl)-2-phenylbenzofuran.

3-(4-Methoxybenzoyl)-2-phenylbenzofuran (16.4 g., 0.05 mol.) is combined with 50 g. of freshly distilled pyridine hydrochloride and the mixture is refluxed 1 hour. The hot mixture is poured with stirring onto an ice-dilute hydrochloric acid mixture and the precipitate is collected to give 3-(4-hydroxybenzoyl)-2-phenylbenzofuran.

A mixture of 6.2 g. (19.7 mmol.) of 3-(4-hydroxybenzoyl)-2-phenylbenzofuran, 2.95 g. (19.7 mmol.) of 3-diethylaminopropyl chloride and 10.9 g. (0.079 mol.) of potassium carbonate in 300 ml. of acetone is refluxed for 12 hours. After cooling, the mixture is filtered and the filtrate is concentrated to give the title compound.

The title compound is dissolved in ether and an ethereal solution of hydrochloric acid is added to give the corresponding hydrochloride salt m.p. 148°–153° (ethyl acetate).

EXAMPLE 2

When 3-(4-hydroxybenzoyl)-2-phenylbenzofuran is reacted with 3-dimethylaminopropyl chloride by the procedure described in Example 1, 3-[4-(3-dimethylaminopropoxy)benzoyl]-2-phenylbenzofuran is obtained.

3-[4-(3-Dimethylaminopropoxy)benzoyl]-2-phenylbenzofuran is converted to the corresponding hydrochloride salt as described in Example 1, m.p. 85°–95° (ethyl acetate).

Similarly, 3-[4-(3-di-n-propylaminopropoxy)benzoyl]-2-phenylbenzofuran is prepared by substitution of 3-di-n-propylaminopropyl chloride in the procedure of Example 1 in place of a 3-diethylaminopropyl chloride.

Treatment of 3-[4-(3-di-n-propylaminopropoxy)benzoyl]-2-phenylbenzofuran with ethereal hydrochloric acid as previously described gives the corresponding hydrochloric acid salt, m.p. 168°′170° (ethyl acetate).

EXAMPLE 3

3-[4-(3-Di-n-butylaminopropoxy)benzoyl]-2-phenylbenzofuran

A mixture of 2.0 g. (6.4 mmol.) of 3-(4-hydroxybenzoyl)-2-phenylbenzofuran, 1.3 g. (6.4 mmol.) of 3-di-n-butylaminopropyl chloride and 4.0 g. (0.04 mol.) of anhydrous potassium carbonate in 20 ml. of dry 2-butanone is refluxed for 18 hours. The reaction is cooled, water and ether are added and the layers are separated. The organic phase is extracted with 10% aqueous sodium hydroxide and the aqueous layers are combined and extracted again with water. The combined ether extracts are concentrated under reduced pressure to give the title compound.

Treatment of the title compound with an ethereal solution of hydrochloric acid as described in Example 1 gives the corresponding hydrochloride salt, m.p. 150°–153° (ethyl acetate).

EXAMPLE 4

3-[4-(4-Diethylaminobutoxy)benzoyl]-2-phenylbenzofuran

A mixture of 3.0 g. (9.5 mmol.) of 3-(4-hydroxybenzoyl)-2-phenylbenzofuran, 6.2 g. (0.029 mol.) of 1,4-dibromobutane and 3.9 g. (0.029 mol.) of potassium carbonate in 100 ml. of dry acetone is refluxed for 18 hours. The reaction mixture is cooled, filtered and the filtrate is concentrated under reduced pressure then heated on a steam bath in vacuo to remove excess 1,4-dibromobutane and leave 3-[4-(4-bromobutoxy)benzoyl]-2-phenylbenzofuran as a residue.

3-[4-(4-Bromobutoxy)benzoyl]-2-phenylbenzofuran (13.0 g., 0.029 mol.) is dissolved in 75 ml. of ethanol containing 8 ml. of diethylamine and refluxed for 24 hours. The solvent is removed under reduced pressure and the residue is dissolved in ether. The ethereal solution is extracted with 5% aqueous sodium hydroxide, water and saturated aqueous sodium chloride solution, dried ($MgSO_4$) and concentrated to give the title compound.

The title compound is converted to the corresponding hydrochloride salt as described in the procedure of Example 1, m.p. 151°–152° (methanol-ether).

EXAMPLE 5

3-[4-(3-Diethylaminopropoxy)-3,5-dimethylbenzoyl]-2-phenylbenzofuran

To a cooled (ice bath) mixture of 10.5 g. (0.054 mol.) of 2-phenylbenzofuran and 11.5 g. (0.058 mol.) of 3,5-dimethyl-4-methoxybenzoyl chloride in 100 ml. of methylene chloride is added dropwise 28.7 g. (0.11 mol.) of stannic chloride. The reaction mixture is allowed to warm to ambient temperature, then stirred for 2 hours. Water is slowly added to the mixture and it is stirred an additional 30 minutes. The layers are separated and the organic phase is washed with water until the washings are neutral, dried ($MgSO_4$) and concentrated to give 3-(3,5-dimethyl-4-methoxybenzoyl)-2-phenylbenzofuran.

3-(3,5-Dimethyl-4-methoxybenzoyl)-2-phenylbenzofuran (17.8 g., 0.05 mol.) is combined with 50 g. of freshly distilled pyridine hydrochloride and the mixture is refluxed 1 hour. The hot mixture is poured with stirring onto an ice-dilute hydrochloric acid mixture and the precipitate is collected to give 3-(3,5-dimethyl-4-hydroxybenzoyl)-2-phenylbenzofuran.

When an equivalent amount of 3-(3,5-dimethyl-4-hydroxybenzoyl)-2-phenylbenzofuran is substituted in the procedure of Example 1 for 3-(4-hydroxybenzoyl)-2-phenylbenzofuran and the reaction mixture is refluxed for 24 hours, the title compound is obtained.

The title compound is converted to the corresponding hydrochloride salt as described in Example 1.

EXAMPLE 6

3-[4-(2-Diethylaminoethoxy)benzoyl]-2-(4-methoxyphenyl)benzofuran

Hydrolysis of ethyl 4-(2-diethylaminoethoxy)benzoate hydrochloride with aqueous concentrated hydrochloric acid at 100° for two hours gives 4-(2-diethylaminoethoxy)benzoic acid hydrochloride, m.p. 166°–168°.

4-(2-Diethylaminoethoxy)benzoic acid hydrochloride is suspended in methylene chloride and a five-fold excess of thionyl chloride is added. The mixture is refluxed until the solid dissolves, then concentrated under reduced pressure to give 4-(2-diethylaminoethoxy)benzoyl chloride hydrochloride.

To a mixture of 11.2 g. (0.05 mol.) of 2-(4-methoxyphenyl)benzofuran and 14.6 g. (0.05 mol.) of 4-(2-diethylaminoethoxy)benzoyl chloride hydrochloride in 100 ml. of methylene chloride is added 39.1 g. (0.15 mol.) of stannic chloride. The reaction mixture is stirred for 1.5 hours at ambient temperature then poured into water. The layers are separated and the organic phase is washed with aqueous sodium carbonate until basic and water, dried (MgSO$_4$) and concentrated to give the title compound.

The title compound is converted to the corresponding hydrochloride salt by the procedure described in Example 1, m.p. 143°–146° (ethyl acetate).

EXAMPLE 7

5-Chloro-3-[4-(2-diethylaminoethoxy)benzoyl]-2-phenylbenzofuran

Acylation of 5-chloro-2-phenylbenzofuran with 4-(2-diethylaminoethoxy)benzoyl chloride hydrochloride as described in the procedure of Example 6 gives the title compound which is converted to the corresponding hydrochloride salt as described in the procedure of Example 1, m.p. 197°–199° (ethyl acetate).

EXAMPLE 8

3-[2-(2-Diethylaminoethoxy)benzoyl]-2-phenylbenzofuran 2-(2-Diethylaminoethoxy)benzoic acid hydrochloride is prepared by hydrolysis of ethyl 2-(2-diethylaminoethoxy)-benzoate hydrochloride as described in Example 6, m.p. 148°–150°.

Reaction of 2-(2-diethylaminoethoxy)benzoate hydrochloride with thionyl chloride as described in the procedure of Example 6 gives 2-(2-diethylaminoethoxy)benzoyl chloride hydrochloride.

Acylation of 2-phenylbenzofuran with 2-(2-diethylaminoethoxy)benzoyl chloride hydrochloride by the procedure described in Example 6 gives the title compound.

Treatment of the title compound with an ethereal solution of hydrochloric acid by the procedure of Example 1 gives the corresponding hydrochloride sale, m.p. 132°–134° (ethyl acetate).

EXAMPLE 9

5-Chloro-3-[2-(2-diethylaminoethoxy)benzoyl]-2-phenylbenzofuran

Acylation of 5-chloro-2-phenylbenzofuran with 2-(2-diethylaminoethoxy)benzoyl chloride hydrochloride by the procedure described in Example 6 gives the title compound.

The title compound is converted to the corresponding hydrochloride salt as described in Example 1, m.p. 160°–162° (ethyl acetate).

EXAMPLE 10

2-(4-Chlorophenyl)-3-[4-(3-diethylaminopropoxy)-benzoyl]benzofuran

When 2-(p-chlorophenyl)benzofuran is acylated with 4-(3-diethylaminopropoxy)benzoyl chloride hydrochloride by the procedure described in Example 6, the title compound is obtained.

Treatment of the title compound with an ethereal solution of hydrochloric acid gives the corresponding hydrochloride salt, m.p. 156°–160° (ethyl acetate).

EXAMPLE 11

3-[4-(3-Diethylaminopropoxy)benzoyl]-2-(4-methoxyphenyl)benzofuran

Acylation of 2-(p-methoxyphenyl)benzofuran with 4-(3-diethylaminopropoxy)benzoyl chloride hydrochloride by the procedure described in Example 6 gives the title compound.

The title compound is converted to the corresponding hydrochloride salt by treatment with an ethereal solution of hydrochloric acid as described above, m.p. 102°–110° (ethyl acetate).

EXAMPLE 12

3-[2-(3-Diethylaminopropoxy)benzoyl]-2-phenylbenzofuran

A mixture of 15.2 g. (0.10 mol.) of methyl salicylate, 16.45 g. (0.11 mol.) of 3-diethylaminopropyl chloride and 27.7 g. (0.20 mol.) of potassium carbonate in 250 ml. of 2-butanone is refluxed for 22 hours to give 2-(2-diethylaminopropoxy)benzoic acid which is converted to the corresponding hydrochloride salt by heating with 100 ml. of concentrated hydrochloric acid for three hours, m.p. 137°–140°.

A mixture of 2.52 g. (8.75 mmol.) of 2-(2-diethylaminopropoxy)benzoic acid hydrochloride and 2.4 ml. of thionyl chloride in 75 ml. of methylene chloride is refluxed for 45 minutes. The mixture is concentrated under reduced pressure and a solution of 1.70 g. (8.75 mmol.) of 2-phenylbenzofuran in 100 ml. of methylene chloride is added. The resulting solution is cooled to 0°, 3.0 ml. of stannic chloride is added and the reaction mixture is stirred for 1.25 hours at 0°, then for 1.25 hours at ambient temperature. The mixture is poured into water, the layers are separated, the aqueous phase is extracted with methylene chloride and the organic phases are combined and washed with 5% aqueous sodium carbonate and water, dried (MgSO$_4$) and concentrated to give the title compound.

The title compound is converted to the corresponding hydrochloride salt as described in Example 1, m.p. 169°–173°.

EXAMPLE 13

5-Chloro-3-[4-(3-diethylaminopropoxy)benzoyl]-2-phenylbenzofuran

5-Chloro-2-phenylbenzofuran is acylated with a p-anisoyl chloride according to the procedure described in Example 5 to give 5-chloro-3-(4-methoxybenzoyl)-2-phenylbenzofuran.

Demethylation of 5-chloro-3-(4-methoxybenzoyl)-2-phenylbenzofuran with pyridine hydrochloride as described above gives 5-chloro-3-(4-hydroxybenzoyl)-2-phenylbenzofuran.

A mixture of 3.2 g. (9.2 mmol.) of 5-chloro-3-(4-hydroxybenzoyl)-2-phenylbenzofuran, 3.5 ml. (0.035mol.) of 1,3-dibromopropane and 4.0 g. (0.029 mol.) of potassium carbonate in 100 ml. of acetone is refluxed for 3 hours. After cooling, the reaction mixture is filtered and the filtrate is concentrated to give 5-chloro-3-[4-(3-bromopropoxy)benzoyl]-2-phenylbenzofuran.

5-Chloro-3-[4-(3-bromopropoxy)benzoyl]-2-phenylbenzofuran (2.0 g., 4.3 mmol.) is refluxed in 100 ml. of ethanol containing 9 ml. of diethylamine for 10 hours. The reaction mixture is concentrated under reduced pressure and the residue is dissolved in ether. The ether solution is washed with aqueous sodium hydroxide and water then concentrated to give the title compound.

The title compound is converted to the corresponding hydrochloride salt by the procedure described in Example 1, m.p. 143°–147° (ethyl acetate).

EXAMPLE 14

3-[4-(3-Diethylaminopropoxy)benzoyl]-2-(4-tolyl)-benzofuran 3-(4-Hydroxybenzoyl)-2-(4-tolyl)benzofuran is prepared by acylation of 2-(4-tolyl)benzofuran with p-anisoyl chloride followed by demethylation of the 3-(4-methoxybenzoyl)-2-(4-tolyl)benzofuran thus formed as described in the procedure of Example 5.

Reaction of 3-(4-hydroxybenzoyl)-2-(4-tolyl)benzofuran with 3-diethylaminopropyl chloride by the procedure described in Example 1 gives the title compound.

EXAMPLE 15

3-[4-(2-Diethylaminoethoxy)benzoyl]-2-(4-tolyl)benzofuran

Reaction of 3-(4-hydroxybenzoyl)-2-(4-tolyl)benzofuran with 2-diethylaminoethyl chloride by the procedure of Example 1 gives the title compound.

The title compound is converted to the corresponding hydrochloride salt by treatment with an ethereal solution of hydrochloric acid as described hereabove, m.p. 148°–151°.

EXAMPLE 16

2-(4-Chlorophenyl)-3-[4-(3-diethylaminopropoxy)-benzoyl]benzofuran

Acylation of 2-(4-chlorophenyl)benzofuran with p-anisoyl chloride followed by demethylation of the 2-(4-chlorophenyl)-3-(4-methoxybenzoyl)benzofuran thus formed by procedures described above gives 2-(4-chlorophenyl)-3-(4-hydroxybenzoyl)benzofuran.

Reaction of 2-(4-chlorophenyl)-3-(4-hydroxybenzoyl)-benzofuran with 3-diethylaminopropyl chloride according to the procedure of Example 1 gives the title compound.

The title compound is treated with an ether solution of hydrochloric acid to give the corresponding hydrochloride salt, m.p. 179°–182°.

EXAMPLE 17

3-[4-(2-Diethylaminoethoxy)benzoyl]-2-phenylbenzofuran

Substitution of an equivalent amount of 2-diethylaminoethyl chloride in the procedure of Example 1 for 3-diethylaminopropyl chloride gives the title compound.

The title compound is converted to the corresponding hydrochloride salt by the procedure described in Example 1, m.p. 125°–127°.

EXAMPLE 18

3-[4-(3-Diethylaminopropoxy)benzoyl]-2-(3,5-dimethylphenyl)-benzofuran

To a cooled (0°) solution of 10.5 g. of cupric sulfate in 40 ml. of 28% ammonium hydroxide and 160 ml. of water is added under a nitrogen atmosphere 5.58 g. (0.08 mol.) of hydroxylamine hydrochloride. A solution of 5.24 g. (0.04 mol.) of 3,5-dimethylphenylacetylene in 200 ml. of ethanol is then added and the reaction mixture is stirred for 15 minutes. The mixture is allowed to warm to ambient temperature and the precipitate is collected by filtration and washed with water, ethanol and ether to give cuprous 3,5-dimethylphenylacetylide.

A flask containing 5.42 g. (0.028 mol.) of cuprous 3,5-dimethylphenylacetylide in 100 ml. of pyridine is thoroughly flushed with nitrogen. A solution of 6.19 g. (0.028 mol.) of o-iodophenol in 50 ml. of pyridine is added under nitrogen and the reaction mixture is stirred and heated at 120° for 22 hours. The pyridine is removed by distillation in vacuo, the residue is added to an ice-water mixture and the gummy precipitate is collected and dissolved in methylene chloride. The methylene chloride solution is washed with 3N hydrochloric acid and water and concentrated under reduced pressure to give a residue which is chromatographed on a silica gel "dry-column" with hexane as the eluant to give 2-(3,5-dimethylphenyl)benzofuran.

Substitution of an equivalent amount of 2-(3,5-dimethylphenyl)benzofuran in the procedure of Example 2 for 2-phenylbenzofuran followed by demethylation of the 2-(3,5-dimethylphenyl)-3-(4-methoxybenzoyl)benzofuran thus formed and reaction of the resulting product with 3-diethylaminopropyl chloride as described therein gives the title compound.

The title compound is converted to the corresponding hydrochloric acid salt as described in Example 1, m.p. 144°–149° (ethyl acetate).

EXAMPLE 19

3-[4-(3-Diethylaminopropoxy)-3,5-dimethylbenzoyl]-2-(3,5-dimethylphenyl)benzofuran When an equivalent amount of 2-(3,5-dimethylphenyl)-benzofuran is used as a starting material in the procedure of Example 5 in place of 2-phenylbenzofuran, the title compound is obtained as the final product.

EXAMPLE 20

Reaction of 2-(3,5-dimethylphenyl)-3-(4-hydroxybenzoyl)benzofuran with 2-diethylaminoethyl chloride by the procedure described in Example 1 for 2-phenyl-3-(4-hydroxybenzoyl)benzofuran and 3-diethylaminopropyl chloride gives 3-[4-(2-diethylaminoethoxy)benzoyl]-2-(3,5-dimethylphenyl)-benzofuran.

In like manner, 3-[4-(3-di-n-butylaminopropoxy)-benzoyl]-2-(3,5-dimethylphenyl)benzofuran is prepared by refluxing 2-(3,5-dimethylphenyl)-3-(4-hydroxybenzoyl)benzofuran with 3-di-n-butylaminopropyl chloride and potassium carbonate in 3-pentanone for 5.5 hours.

EXAMPLE 21

2-[4-(2-Diethylaminoethoxy)benzoyl]-3-phenylbenzofuran

Acylation of 3-phenylbenzofuran with p-anisoyl chloride over a 4 hour period as described in the procedure of Example 1 followed by demethylation of the 2-(4-methoxybenzoyl)-3-phenylbenzofuran thus formed as previously described gives 2-(4-hydroxybenzoyl)-3-phenylbenzofuran.

Reaction of 1.6 g. (0.005 mol.) of 2-(4-hydroxybenzoyl)-3-phenylbenzofuran with 2.7 g. (0.02 mol.) of 2-diethylaminoethyl chloride in 50 ml. of acetone containing 2.7 g. (0.02 mol.) of potassium carbonate for 3 hours according to the procedure described in Example 1 gives the title compound.

The title compound is converted to the corresponding hydrochloride salt as previously described, m.p. 155°–159° (ethyl acetate).

EXAMPLE 22

2-[4-(3-Diethylaminopropoxy)benzoyl]-3-phenylbenzofuran

Reaction of 2-(4-hydroxybenzoyl)-3-phenylbenzofuran with 1,3-dibromopropane according to the procedure of Example 4 gives 2-[4-(3-bromopropoxy)benzoyl]-3-phenylbenzofuran.

2-[4-(3-Bromopropoxy)benzoyl]-3-phenylbenzofuran (2.5 g., 5.7 mmol.) is refluxed for 6 hours in 50 ml. of ethanol containing 20 ml. of diethylamine. The reaction mixture is concentrated under reduced pressure and the residue is dissolved in chloroform. The chloroform solution is washed with water, saturated aqueous sodium chloride solution and water, dried (MgSO$_4$) and concentrated to give the title compound.

Addition of an ethereal solution of hydrochloric acid to a solution of the title compound in chloroform gives the correspondinig hydrochloride salt which is purified by chromatography on silica gel, m.p. 122°–126° (ethyl acetate-ether).

EXAMPLE 23

3-(4-Chlorophenyl)-2-[4-(3-diethylaminopropoxy)benzoyl]benzofuran

A mixture of 23.3 g. (0.1 mol.) of α-bromo-p-chloroacetophenone, 10.0 g. (0.1 mol.) of phenol and 14.5 g. (0.1 mol.) of potassium carbonate in 65 ml. of dry acetone is refluxed for 12 hours. The reaction mixture is cooled, poured into 500 ml. of water and the precipitate formed is collected by filtration and recrystallized from ethanol to give α-phenoxy-p-chloroacetophenone.

α-Phenoxy-p-chloroacetophenone (11.0 g., 0.045 mol.) is added to 90 g. of polyphosphoric acid preheated to 80° and the mixture is stirred for 12 hours. The reaction mixture is poured into 800 ml. of water and the aqueous mixture is extracted 3 times with ether. The combined extracts are washed with water, saturated aqueous sodium bicarbonate solution and saturated aqueous sodium chloride solution, dried (MgSO$_4$) and concentrated under reduced pressure to give 3-(4-chlorophenyl)benzofuran, m.p. 56°–57°.

Acylation of 3-(4-chlorophenyl)benzofuran with p-anisoyl chloride as described in Example 21 for 3-phenylbenzofuran followed by demethylation of the product formed with pyridine hydrochloride as previously described gives 3-(4-chlorophenyl)-2-(4-hydroxybenzoyl)benzofuran, m.p. 220°–221° (ethyl acetate).

Reaction of 3.0 g. (0.009 mol.) of 3-(4-chlorophenyl)-2-(4-hydroxybenzoyl)benzofuran with 1.4 g. (0.009 mol.) of 3-diethylaminopropyl chloride in 50 ml. of dry 3-pentanone containing 5.2 g. (0.04 mol.) of potassium carbonate by the method described in Example 1 gives the title compound.

The title compound is converted to the corresponding hydrochloride salt as described hereinabove, m.p. 165°–168°.

EXAMPLE 24

2-(4-Chlorobenzyl)-3-[4-(2-diethylaminoethoxy)benzoyl]benzofuran

To a solution of 15.3 g. (0.125 mol.) of salicylaldehyde in 100 ml. of acetone is added 7.0 g. (0.125 mol.) of potassium hydroxide dissolved in a minimum amount of water. α-Bromo-p-chloroacetophenone (29.16 g., 0.125 mol.) is added dropwise with stirring and cooling (ice bath). After addition, the reaction mixture is stirred at 25° for 12 hours. The precipitate is collected by filtration, washed with water and combined with the residue remaining after concentration of the filtrate to give an intermediate which is immediately dehydrated by refluxing in toluene with 0.2 g. of p-toluenesulfonic acid to yield 2-(4-chlorobenzoyl)benzofuran.

Hydrazine hydrate (28.0 g., 0.5 mol.) is added to a solution of 42.0 g. (0.16 mol.) of 2-(4-chlorobenzoyl)benzofuran in 400 ml. of ethanol and the reaction mixture is refluxed overnight. The solution is concentrated under reduced pressure, chloroform is added and the chloroform solution is washed with saturated aqueous sodium chloride, dried (MgSO$_4$) and concentrated to yield the corresponding hydrazone. The hydrazone is dissolved in 100 ml. of dry dimethyl sulfoxide and added dropwise over a 4 hour interval to a slurry of 36.4 g. (0.32 mol.) of potassium t-butoxide in 100 ml. of dry dimethyl sulfoxide. The reaction mixture is poured into 500 ml. of water and the aqueous solution is extracted with chloroform. The extracts are washed with water, dried (MgSO$_4$) and concentrated in vacuo to give 2-(4-chlorobenzyl)benzofuran which is purified by chromatography on silica gel with carbon tetrachloride as eluant.

Acylation of 2-(4-chlorobenzyl)benzofuran with p-anisoyl chloride is accomplished as described in Example 1. Demethylation with pyridine hydrochloride as previously described gives 2-(4-chlorobenzyl)-3-(4-hydroxybenzoyl)benzofuran.

A solution of 2-(4-chlorobenzyl)-3-(4-hydroxybenzoyl)benzofuran (2.0 g., 5.5 mmol) of 50 ml. of toluene is added to a slurry of 0.5 g. of a 57% sodium hydride dispersion (0.01 mol.) in 5 ml. of toluene. The reaction mixture is refluxed for 10 minutes, then 0.82 g. (5.5 mmol.) of 2-diethylaminoethyl chloride is added and the mixture is heated at 90° for 4 hours. The mixture is filtered and the filtrate concentrated under reduced pressure to give the title compound.

The title compound is converted to the corresponding hydrochloride salt by treatment with an ethereal solution of hydrochloric acid as described above, m.p. 148°–150° (chloroform-ether).

EXAMPLE 25

2-(4-Chlorobenzyl)-3-[4-(3-diethylaminopropoxy)-benzoyl]benzofuran

Substitution of an equivalent amount of 2-(4-chlorobenzyl)-3-(4-hydroxybenzoyl)benzofuran in the procedure of Example 1 for 3-(4-hydroxybenzoyl)-2-phenylbenzofuran gives the title compound.

EXAMPLE 26

3-[4-(3-Diethylaminopropoxy)benzoyl]-2-(3-trifluoromethylbenzyl)benzofuran

To a solution of 24.8 g. (0.127 mol.) of m-trifluoromethylacetophenone in 20 ml. of anhydrous ether is added with cooling and stirring 0.15 g. of anhydrous aluminum chloride and 20.2 g. (0.127 mol.) of bromine. The reaction mixture is concentrated and the residue is distilled to give α-bromo-m-trifluoromethylacetophenone, b.p. 135°–140° (20 mm.)

Substitution of an equivalent amount of α-bromo-m-trifluoromethylacetophenone in the procedure of Example 24 for α-bromo-p-chloroacetophenone followed by treatment of the 2-(3-trifluoromethylbenzoyl)benzofuran with hydrazine hydrate ultimately gives 2-(3-trifluoromethylbenzyl)benzofuran, b.p. 195°–197° (25 mm.).

Acylation of 2-(3-trifluoromethylbenzyl)benzofuran with p-anisoyl chloride is carried out as outlined in the procedure of Example 1 to give 3-(4-methoxybenzoyl)-2-(3-trifluoromethylbenzyl)benzofuran.

Demethylation of 3-(4-methoxybenzoyl)-2-(3-trifluoromethylbenzyl)benzofuran followed by reaction of the 3-(4-hydroxybenzoyl)-2-(3-trifluoromethylbenzyl)benzofuran thus formed with 3-diethylminopropyl chloride as described in the procedure of Example 1 gives the title compound.

The title compound is converted to the corresponding hydrochloride salt as described in Example 1.

EXAMPLE 27

3-[3-Methyl-4-(3-diethylaminopropoxy)benzoyl]-2-phenylbenzofuran

A solution of 11.5 g. (0.07 mol.) of 3-methyl-4-methoxybenzoic acid and 10.7 g. (0.09 mol.) of thionyl chloride in 60 ml. of methylene chloride is refluxed on a steam bath for two hours. Concentration under reduced pressure and distillation of the residue gives 3-methyl-4-methoxybenzoic acid chloride, m.p. 37°–39°.

To a cooled, stirred solution of 10.8 g. (0.058 mol.) of 3-methyl-4-methoxybenzoic acid chloride and 9.6 g. (0.054 mol.) of 2-phenylbenzofuran in 40 ml. of carbon disulfide is added dropwise over a 20 minute interval 28.2 g. (0.108 mol.) of stannic chloride. After addition, the reaction mixture is warmed to ambient temperature and stirred for 2 hours. The mixture is then poured onto 100 ml. of ice-water and stirred for 1 hour. The solvent is removed, and the product extracted into chloroform and the extracts are washed with water, dried ($Na_2SO_4$) and concentrated under reduced pressure to give 3-(3-methyl-4-methoxybenzoyl)-2-phenylbenzofuran.

Demethylation of 3-(3-methyl-4-methoxybenzoyl)-2-phenylbenzofuran gives 3-(3-methyl-4-hydroxybenzoyl)-2-phenylbenzofuran which, when substituted in the procedure of Example 1 for 3-(4-hydroxybenzoyl)-2-phenylbenzofuran in the reaction with 3-diethylaminopropyl chloride, gives the title compound.

EXAMPLE 28

3-[3-(3-Diethylaminopropoxy)benzoyl]-2-phenylbenzofuran

Acylation of 10.5 g. (0.054 mol.) of 2-phenylbenzofuran with 9.9 g. (0.058 mol.) of m-anisoyl chloride according to the procedure described in Example 1 gives 3-(3-methoxybenzoyl)-2-phenylbenzofuran.

Demethylation of 3-(3-methoxybenzoyl)-2-phenylbenzofuran followed by reaction of 3-(3-hydroxybenzoyl)-2-phenylbenzofuran with 3-diethylaminopropyl chloride as described in Example 1 gives the title compound.

EXAMPLE 29

2-Benzyl-3-[4-(3-diethylaminopropoxy)benzoyl]benzofuran

When an equivalent amount of 2-benzylbenzofuran is used as a starting material in the procedure of Example 1 in place of 2-phenylbenzofuran, the title compound is ultimately prepared.

EXAMPLE 30

Substitution of an equivalent amount of 2-fluorophenylacetylene in the procedure of Example 18 for 3,5-dimethylphenylacetylene give cuprous 2-fluorophenylacetylide.

Reaction of cuprous 2-fluorophenylacetylide with o-iodophenol as described in Example 18 gives 2-(2-fluorophenyl)benzofuran.

Substitution of an equivalent amount of 2-(2-fluorophenyl)benzofuran in the procedure of Example 1 for 2-phenylbenzofuran followed by demethylation of the 2-(2-fluorophenyl)-3-(4-methoxybenzoyl)benzofuran thus formed and reaction of the resulting product with 3-diethylaminopropyl chloride as described therein gives 3-[4-(3-diethylaminopropoxy)benzoyl]-2-fluorophenyl)benzofuran.

Similarly, when 2,4,6-triisopropylphenylacetylene is used as a starting material in the procedure of Example 18 in place of 3,5-dimethylphenylacetylene, 3-[4-(3-diethylaminopropoxy)benzoyl]-2-(2,4,6-triisopropylphenyl)benzofuran is obtained as the final product.

EXAMPLE 31

3-[3,5-Di-t-butyl-4-(3-diethylaminopropoxy)benzoyl]-2-phenylbenzofuran 3,5-Di-t-butyl-4-hydroxybenzoic acid is refluxed with thionyl chloride as described in the procedure of Example 27 to give 3,5-di-t-butyl-4-hydroxybenzoyl chloride.

Acylation of 2-phenylbenzofuran with 3,5-di-t-butyl-4-hydroxybenzoyl chloride as described above gives 3-(3,5-di-t-butyl-4-hydroxybenzoyl)-2-phenylbenzofuran which, upon reaction with 3-diethylaminopropyl chloride and potassium hydroxide in ethanol according to procedures described above, gives the title compound.

EXAMPLE 32

3-[3-Methoxy-4-(3-diethylaminopropoxy)benzoyl]-2-phenylbenzofuran

A mixture of 19.4 g. (0.1 mol.) of 2-phenylbenzofuran and 19.1 g. (0.1 mol.) of 4-acetoxy-3-methoxybenzonitrile in 20 ml. of trifluoroacetic acid is refluxed for 3 hours. The reaction mixture is cooled, diluted with 200 ml. of water and the resulting aqueous solution is extracted with ether. The extracts are concentrated to dryness and the residue is dissolved in 100 ml. of ethanol and heated with 20 ml. of 10% aqueous sodium carbonate for 2 hours. The mixture is concentrated, the residue extracted with ether and the extracts are dried and concentrated to give 3-(3-methoxy-4-hydroxybenzoyl)-2-phenylbenzofuran.

Reaction of 3-(3-methoxy-4-hydroxybenzoyl)-2-phenylbenzofuran with 3-diethylaminopropyl chloride according to the procedure of Example 1 gives the title compound.

EXAMPLE 33

Substitution of a substituted acetophenone listed below:
α-bromo-4-methoxyacetophenone
α-bromo-2-methoxyacetophenone
α-bromo-2,5-dimethoxyacetophenone
α-bromo-4-methylacetophenone
α-bromo-4-ethylacetophenone
α-chloro-4-fluoroacetophenone in the procedure of Example 24 for α-bromo-p-chloroacetophenone followed by reduction of the product benzoylbenzofuran with hydrazine hydrate as described therein gives the following benzylbenzofurans:
2-(4-methoxybenzyl)benzofuran
2-(2-methoxybenzyl)benzofuran
2-(2,5-dimethoxybenzyl)benzofuran
2-(4-methylbenzyl)benzofuran
2-(4-ethylbenzyl)benzofuran
2-(4-fluorobenzyl)benzofuran.

Acylation of the benzylbenzofurans listed above with 4-(2-diethylaminoethoxy)benzoyl chloride hydrochloride as described in the procedure of Example 6 gives the following compounds of this invention, respectively:
3-[4-(2-diethylaminoethoxy)benzoyl]-2-(4-methoxybenzyl)-benzofuran
3-[4-(2-diethylaminoethoxy)benzoyl]-2-(2-methoxybenzyl)benzofuran
3-[4-(2-diethylaminoethoxy)benzoyl]-2-(2,5-dimethoxybenzyl)benzofuran
3-[4-(2-diethylaminoethoxy)benzoyl]-2-(4-methylbenzyl)benzofuran
3-[4-(2-diethylaminoethoxy)benzoyl]-2-(4-ethylbenzyl)benzofuran
3-[4-(2-diethylaminoethoxy)benzoyl]-2-(4-fluorobenzyl)benzofuran.

EXAMPLE 34

2-Benzyl-5-bromo-3-[4-(3-diethylaminopropoxy)benzoyl]benzofuran

A mixture of 35.5 g. (0.18 mol.) of 5-bromobenzofuran, 45.2 g. (0.18 mol.) of benzoic anhydride, 24.4 g. (0.20 mol.) of benzoic acid and 5 g. (0.05 mol.) of phosphoric acid is refluxed for 4 hours then stirred at 25° for 12 hours. The reaction mixture is basicified with 10% aqueous sodium hydroxide, chloroform is added to the mixture and the layers are separated. The organic phase is washed with water, dried (MgSO₄) and concentrated under reduced pressure to give 2-benzoyl-5-bromobenzofuran.

A mixture of 42.2 g. (0.14 mol.) of 2-benzoyl-5-bromobenzofuran and 35 ml. of 98% hydrazine in 70 ml. of diethylene glycol is warmed for a few minutes on a steam bath. Then 23.3 g. of potassium hydroxide is added and the reaction mixture is refluxed for 2 hours. After cooling, water is added to the mixture and the resulting aqueous solution is extracted with benzene. The extract is washed with water, 10% aqueous hydrochloric acid and water, dried (MgSO₄) and concentrated to yield 2-benzyl-5-bromobenzofuran.

2-Benzyl-5-bromobenzofuran is acylated with p-anisoyl chloride as described above and the resulting 2-benzyl-5-bromo-3-(4-methoxybenzoyl)benzofuran is demethylated and the product reacted with 3-diethylaminopropyl chloride as previously described to give the title compound.

EXAMPLE 35

When a benzofuran listed below:
6-chlorobenzofuran
7-chlorobenzofuran
4-methylbenzofuran
5-ethylbenzofuran is used as a starting material in the procedure of Example 34 in place of 5-bromobenzofuran, the following compounds of this invention are obtained as final products:
2-benzyl-6-chloro-3-[4-(3-diethylaminopropoxy)benzoyl]benzofuran
2-benzyl-7-chloro-3-[4-(3-diethylaminopropoxy)benzoyl]benzofuran
2-benzyl-3-[4-(3-diethylaminopropoxy)benzoyl]-4-methylbenzofuran
2-benzyl-3-[4-(3-diethylaminopropoxy)benzoyl]-5-ethylbenzofuran.

EXAMPLE 36

Substitution of an equivalent amount of 4-methoxybenzofuran in the procedure of Example 34 for 5-bromobenzofuran followed by reduction of the 2-benzoyl-4-methoxybenzofuran with hydrazine as described therein gives 2-benzyl-4-methoxybenzofuran.

Acylation of 2-benzyl-4-methoxybenzofuran with 4-(2-diethylaminoethoxy)benzoyl chloride hydrochloride as described in Example 6 gives 2-benzyl-3-[4-(2-diethylaminoethoxy)benzoyl]-4-methoxybenzofuran.

In like manner, when 5-methoxybenzofuran is used as a starting material in the procedure of Example 34 and the resulting 2-benzyl-5-methoxybenzofuran is acylated with 4-(2-diethylaminoethoxy)benzoyl chloride hydrochloride, 2-benzyl-3-[4-(2-diethylaminoethoxy)benzoyl]-5-methoxybenzofuran is obtained.

EXAMPLE 37

3-[4-(2-Diethylaminoethoxy)benzoyl]-2-(4-ethoxybenzyl)benzofuran

Acylation of 2-p-ethoxybenzylbensofuran with 4-(2-diethylaminoethoxy)benzoyl chloride hydrochloride according to the procedure described in Example 6 gives the title compound.

EXAMPLE 38

3-[3,5-Diethyl-4-(3-diethylaminopropoxy)benzoyl]-2-phenylbenzofuran

A solution of 27.2 g. (0.14 mol.) of 3,5-diethyl-4-hydroxybenzoic acid in 200 ml. of methanol containing 2 ml. of sulfuric acid is refluxed for 12 hours. After cooling, excess methanol is evaporated, water is added to the residue and it is made basic with 10% aqueous sodium hydroxide. The precipitate is collected, washed with water and dried in vacuo to give 3,5-diethyl-4-hydroxybenzoic acid methyl ester.

To a cooled solution of 16.2 g. (0.078 mol.) of 3,5-diethyl-4-hydroxybenzoic acid methyl ester and 4.0 g. (0.1 mol.) of sodium hydroxide in 100 ml. of water is added 9.8 g. (7.3 ml., 0.079 mol.) of dimethyl sulfate. The reaction mixture is refluxed for 2 hours. After cooling, ether is added and the layers are separated. The organic phase is washed with water, dilute sulfuric acid and water, dried ($Na_2SO_4$) and concentrated to give 3,5-diethyl-4-methoxybenzoic acid methyl ester.

A mixture of 11.6 g. (0.052 mol.) of 3,5-diethyl-4-methoxybenzoic acid methyl ester and 3.5 g. (0.09 mol.) of sodium hydroxide in 150 ml. of water is refluxed for 2 hours. The reaction mixture is cooled and acidified with 10% aqueous hydrochloric acid to give 3,5-diethyl-4-methoxybenzoic acid. The acid is refluxed with thionyl chloride as described in the procedure of Example 27 to give 3,5-diethyl-4-methoxybenzoyl chloride.

3-(3,5-Diethyl-4-methoxybenzoyl)-2-phenylbenzofuran is prepared by acylation of 2-phenylbenzofuran with 3,5-diethyl-4-methoxybenzoyl chloride as described above. The subsequent steps of demethylation and reaction with 3-diethyl-aminopropyl chloride to give the title compound are accomplished as previously described.

EXAMPLE 39

The following substituted benzoic acids:
3,5-diethoxy-4-hydroxybenzoic acid
3,5-dimethoxy-4-hydroxybenzoic acid
3-ethoxy-4-hydroxybenzoic acid
3-isopropoxy-4-hydroxybenzoic acid
are esterified with methanol according to the procedure described in Example 38 to give the corresponding methyl esters.

Reaction of the methyl esters with 3-diethylaminopropyl chloride with subsequent hydrolysis of the esters by procedures described hereinabove followed by reaction of the acids thus formed with thionyl chloride gives the substituted benzoyl chlorides listed below:
3,5-diethoxy-4-(3-diethylaminopropoxy)benzoyl chloride
4-(3-diethylaminopropoxy)-3,5-dimethoxybenzoyl chloride
4-(3-diethylaminopropoxy)-3-ethoxybenzoyl chloride
4-(3-diethylaminopropoxy)-3-isopropoxybenzoyl chloride.

Acylation of 2-phenylbenzofuran with a substituted benzoyl chloride listed above or its corresponding hydrochloride salt by the procedures of Examples 5 or 6 gives the following compounds of this invention:
3-[3,5-diethoxy-4-(3-diethylaminopropoxy)benzoyl]-2-phenylbenzofuran
3-[4-(3-diethylaminopropoxy)-3,5-dimethoxybenzoyl]-2-phenylbenzofuran
3-[4-(3-diethylaminopropoxy)-3-ethoxybenzoyl]-2-phenylbenzofuran
3-[4-(3-diethylaminopropoxy)-3-isopropoxybenzoyl]-2-phenylbenzofuran.

EXAMPLE 40

When a substituted phenol listed below:
4-fluorophenol
3-trifluoromethylphenol
3-nitrophenol
4-n-propylphenol
4-n-butoxyphenol
is reacted with α-bromoacetophenone according to the procedure described in Example 23 and the resulting product is cyclized by heating with polyphosphoric acid at 80° as described therein, the following benzofurans are obtained:
5-fluoro-3-phenylbenzofuran
3-phenyl-4-trifluoromethylbenzofuran
4-nitro-3-phenylbenzofuran
3-phenyl-5-n-propylbenzofuran
5-n-butoxy-3-phenylbenzofuran.

Acylation of a substituted benzofuran listed above with 4-(2-diethylaminoethoxy)benzoyl chloride hydrochloride as described hereinabove gives the following compounds of this invention:
2-[4-(2-diethylaminoethoxy)benzoyl]-5-fluoro-3-phenylbenzofuran
2-[4-(2-diethylaminoethoxy)benzoyl]-3-phenyl-4-trifluoromethylbenzofuran
2-[4-(2-diethylaminoethoxy)benzoyl]-4-nitro-3-phenylbenzofuran
2-[4-(2-diethylaminoethoxy)benzoyl]-3-phenyl-5-n-propylbenzofuran
5-n-butoxy-2-[4-(2-diethylaminoethoxy)benzoyl]-3-phenylbenzofuran.

EXAMPLE 41

3-[4-(3-Diethylaminopropoxy)benzoyl]-2-(4-ethylphenyl)benzofuran

A mixture of 4.94 g. (0.015 mol.) of carbon tetrabromide, 3.90 g. (0.015 mol.) of triphenylphosphine and 0.975 g. (0.015 g.-atom) of zinc in 25 ml. of carbon tetrachloride is stirred at 25° for 24 hours. A solution of 1.0 g. (7.45 mmol.) of p-ethylbenzaldehyde in 10 ml. of methylene chloride is added and the reaction mixture is stirred an additional 2 hours. Petroleum ether (140 ml.) is added to the mixture, the organic layer is decanted and the residue is extracted with 1:4 methylene chloride-petroleum ether. The combined organic solutions are concentrated under reduced pressure to give 1,1-dibromo-2-(4-ethylphenyl)ethylene.

1,1-Dibromo-2-(4-ethylphenyl)ethylene (1.1 g., 3.69 mmol.) is dissolved in 20 ml. of dry tetrahydrofuran and maintained under a nitrogen atmosphere. The solution is cooled to −78° and 3.9 ml. of a 1.9 M solution of butyl lithium in hexane is added with stirring. The reaction mixture is stirred 1 hour at −78°, then warmed to ambient temperature and stirred an additional hour. Water is added, the mixture is extracted with petroleum ether, the extracts are combined, dried ($MgSO_4$) and concentrated to give 4-ethylphenylacetylene.

Substitution of an equivalent amount of 4-ethylphenylacetylene in the procedure of Example 18 for 3,5-dimethylphenylacetylene followed by reaction of the cuprous 4-ethylphenylacetylide thus obtained with o-iodophenol as described therein gives 2-(4-ethylphenyl)benzofuran.

Acylation of 2-(4-ethylphenyl)benzofuran with 4-(3-diethylaminopropoxy)benzoyl chloride hydrochloride as described above gives the title compound.

EXAMPLE 42

When a substituted benzaldehyde listed below:

3-t-butylbenzaldehyde
2,4,5-trimethylbenzaldehyde
p-fluorobenzaldehyde
2,4-dibromobenzaldehyde
3,4-dichlorobenzaldehyde
3,5-dichlorobenzaldehyde
2,4,6-trichlorobenzaldehyde
o-ethoxybenzaldehyde
p-propoxybenzaldehyde
2-sec-butoxybenzaldehyde
3,4-dimethoxybenzaldehyde
2,4,6-trimethoxybenzaldehyde
3,4,5-trimethoxybenzaldehyde
α,α,α-trifluoro-p-tolualdehyde is used as a starting material in the procedure of Example 41 in place of p-ethylbenzaldehyde, the product phenylacetylenes are substituted in the procedure of Example 18 to give the corresponding cuprous phenylacetylides and the cuprous phenylacetylides are reacted with o-iodophenol as described in Example 18, the following benzofurans are obtained, respectively:

2-(3-t-butylphenyl)benzofuran
2-(2,4,5-trimethylphenyl)benzofuran
2-(4-fluorophenyl)benzofuran
2-(2,4-dibromophenyl)benzofuran
2-(3,4-dichlorophenyl)benzofuran
2-(3,5-dichlorophenyl)benzofuran
2-(2,4,6-trichlorophenyl)benzofuran
2-(2-ethoxyphenyl)benzofuran
2-(4-propoxyphenyl)benzofuran
2-(2-sec-butoxyphenyl)benzofuran
2-(3,4-dimethoxyphenyl)benzofuran
2-(2,4,6-trimethoxyphenyl)benzofuran
2-(3,4,5-trimethoxyphenyl)benzofuran
2-(4-trifluoromethylphenyl)benzofuran.

Acylation of a 2-substituted benzofuran listed above with 4-(3-diethylaminopropoxy)benzoyl chloride hydrochloride as described hereinabove gives the compounds of this invention listed below:

2-(3-t-butylphenyl)-3-[4-(3-diethylaminopropoxy)-
benzoyl]benzofuran
3-[4-(3-diethylaminopropoxy)benzoyl]-2-(2,4,5-
trimethylphenyl)benzofuran
3-[4-(3-diethylaminopropoxy)benzoyl]-2-(4-fluoro-
phenyl)benzofuran
2-(2,4-dibromophenyl)-3-[4-(3-diethylamino-
propoxy)benzoyl]benzofuran
2-(3,4-dichlorophenyl)-3-[4-(3-diethylamino-
propoxy)benzoyl]benzofuran
2-(3,5-dichlorophenyl)-3-[4-(3-diethylamino-
propoxy)benzoyl]benzofuran
3-[4-(3-diethylaminopropoxy)benzoyl]-2-(2,4,6-tri-
chlorophenyl)benzofuran
3-[4-(3-diethylaminopropoxy)benzoyl]-2-(2-ethoxy-
phenyl)benzofuran
3-[4-(3-diethylaminopropoxy)benzoyl]-2-(4-
propoxyphenyl)benzofuran
2-(2-sec-butoxyphenyl)-3-[4-(3-diethylamino-
propoxy)benzoyl]benzofuran
3-[4-(3-diethylaminopropoxy)benzoyl]-2-(3,4-dime-
thoxyphenyl)benzofuran
3-[4-(3-diethylaminopropoxy)benzoyl]-2-(2,4,6-
trimethoxyphenyl)benzofuran
3-[4-(3-diethylaminopropoxy)benzoyl]-2-(3,4,5-
trimethoxyphenyl)benzofuran
3-[4-(3-diethylaminopropoxy)benzoyl]-2-(4-tri-
fluoromethylphenyl)benzofuran.

EXAMPLE 43

Reaction of 3-[4-(4-bromobutoxy)benzoyl]-2-phenylbenzofuran with methylamine according to the procedure described in Example 4 gives 3-[4-(4-methylaminobutoxy)benzoyl]-2-phenylbenzofuran.

Similarly, substitution of propylamine or butylamine in the procedure of Example 4 for diethylamine gives 3-[4-(4-n-propylaminobutoxy)benzoyl]-2-phenylbenzofuran and 3-[4-(4-n-butylaminobutoxy)benzoyl]-2-phenylbenzofuran, respectively.

EXAMPLE 44

5-Chloro-3-[4-(3-di-n-propylaminopropoxy)benzoyl]-
2-(4-methoxyphenyl)benzofuran Substitution of p-methoxyphenylacetylene in the procedure of Example 18 in place of 3,5-dimethylphenylacetylene gives cuprous p-methoxyphenylacetylide.

Reaction of cuprous p-methoxyphenylacetylide with 2-bromo-4-chlorophenyl as described in Example 18 gives 5-chloro-2-(4-methoxyphenyl)benzofuran which upon acylation with 4-(3-di-n-propylaminopropoxy)-benzoyl chloride hydrochloride, prepared from methyl p-hydroxybenzoate and 3-di-n-propylaminopropyl chloride as described hereinabove, gives the title compound.

EXAMPLE 45

3-[4-(3-Diethylaminopropoxy)benzoyl]-2-phenylbenzothiophene

To a slurry of 4.0 g. (0.03 mol.) of anhydrous aluminum chloride in 30 ml. of carbon disulfide under a nitrogen atmosphere at 5° is added a mixture of 2.1 g. (0.01 mol.) of 2-phenylbenzothiophene in 40 ml. of 1:1 carbon disulfide-methylene chloride containing 3.06 g. (0.01 mol.) of 4-(3-diethylaminopropoxy)benzoyl chloride. After addition, the reaction mixture is warmed to ambient temperature and stirred for 16 hours. Dilute aqueous hydrochloric acid is added to the mixture and the layers are separated. The aqueous phase is re-extracted with chloroform and the organic layers are combined and concentrated to give a residue which is treated with ethereal hydrochloric acid and chromatographed on silica gel with methanol-chloroform as eluant to give the title compound as the corresponding hydrochloride salt.

EXAMPLE 46

When an equivalent amount of a benzothiophene listed below:

3-phenylbenzothiophene
2-benzylbenzothiophene
5-chloro-3-phenylbenzothiophene
2-(4-methoxyphenyl)benzothiophene is used as a starting material in the procedure of Example 45 in place of 2-phenylbenzothiophene, the following compounds of this invention are obtained and isolated as the corresponding hydrochloride salts:

2-[4-(3-diethylaminopropoxy)benzoyl]-3-phenyl-
benzothiophene
2-benzyl-3-[4-(3-diethylaminopropoxy)benzoyl]-
benzothiophene
5-chloro-2-[4-(3-diethylaminopropoxy)benzoyl]-3-
phenylbenzothiophene
3-[4-(3-diethylaminopropoxy)benzoyl]-2-(4-
methoxyphenyl)benzothiophene.

EXAMPLE 47

Addition of an ethereal solution of oxalic acid to a solution of 3-[4-(3-diethylaminopropoxy)benzoyl]-2-phenylbenzofuran in ether gives the oxalate salt.

The corresponding hydrochloride salt may be prepared from the oxalate salt by passage of a solution of 3-[4-(3-diethylaminopropoxy)benzoyl]-2-phenylbenzofuran oxalate in ethanol through an Amberlite IRA-401 chloride ion exchange column.

In a similar manner, other acid addition salts may be prepared.

EXAMPLE 48

| Ingredients | Amounts |
| --- | --- |
| 3-[4-(3-Diethylaminopropoxy)benzoyl]-2-phenylbenzofuran | 100 mg. |
| Calcium sulfate dihydrate | 150 mg. |
| Sucrose | 25 mg. |
| Starch | 15 mg. |
| Talc | 5 mg. |
| Stearic acid | 3 mg. |

The sucrose, calcium sulfate dihydrate and 3-[4-(3-diethylaminopropoxy)benzoyl]-2-phenylbenzofuran are thoroughly mixed and granulated with 10% gelatin solution. The wet granules are screened, dried and then mixed with the starch, talc and stearic acid, screened and compressed into a tablet.

EXAMPLE 49

| Ingredients | Amounts |
| --- | --- |
| 3-[4-(3-Diethylaminopropoxy)benzoyl]-2-phenylbenzofuran | 150 mg. |
| Magnesium stearate | 5 mg. |
| Lactose | 100 mg. |

The ingredients are mixed and filled into a hard gelatin capsule.

Similarly, the other substituted benzofurans disclosed herein may be formulated into tablets and capsules by the procedures of Examples 48 and 49.

The compositions prepared as in Examples 48 and 49 are administered orally to a subject in need of coronary vasodilator activity within the dose ranges given hereabove.

What is claimed is:

1. A compound of the formula:

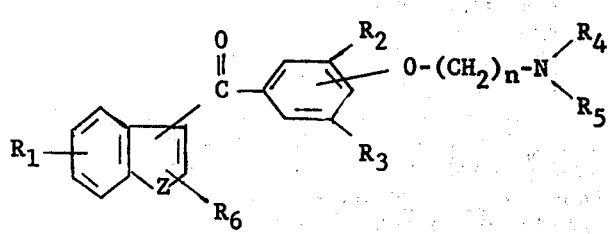

or a pharmaceutically acceptable acid addition salt thereof, in which:

$R_1$ is hydrogen, halo, trifluoromethyl, nitro, lower alkyl or lower alkoxy;

$R_2$ and $R_3$ are hydrogen, lower alkyl or lower alkoxy;

$R_4$ is hydrogen or straight chain lower alkyl;

$R_5$ is straight chain lower alkyl;

$R_6$ is phenyl, lower alkylphenyl, di-lower alkylphenyl, tri-lower alkylphenyl, lower alkoxyphenyl, di-lower alkoxyphenyl, tri-lower alkoxyphenyl, halophenyl, dihalophenyl, trihalophenyl, trifluoromethylphenyl, benzyl, halobenzyl, lower alkylbenzyl, lower alkoxybenzyl or trifluoromethylbenzyl;

$n$ is 2 to 4; and

Z is sulfur.

2. A compound of the formula:

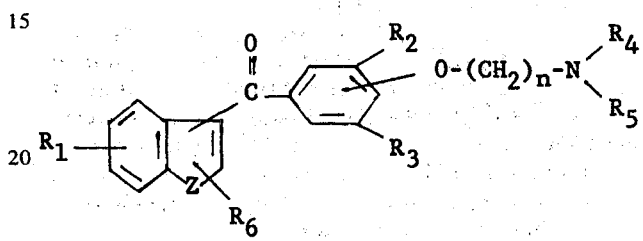

or a pharmaceutically acceptable acid addition salt thereof, in which the aminoalkoxy side chain is in the para position of the benzoyl ring; $R_1$ is hydrogen or halo in the 5-position; $R_2$ and $R_3$ are hydrogen; $R_4$ and $R_5$ are ethyl, n-propyl or n-butyl; $R_6$ is tolyl, chlorophenyl, bromophenyl, methoxyphenyl, trifluoromethylphenyl, dimethylphenyl, dichlorophenyl, dimethoxyphenyl, trimethoxyphenyl, chlorobenzyl or trifluoromethylbenzyl; $n$ is 2 to 4 and Z is oxygen or sulphur.

3. A compound according to claim 2 in which $R_1$ is hydrogen or chloro in the 5-position; $R_6$ is p-tolyl, p-chlorophenyl, p-methoxyphenyl, 3,5-dimethylphenyl, 3,4-dichlorophenyl, 3,4-dimethoxyphenyl, 3,4,5-trimethoxyphenyl, p-chlorobenzyl or m-trifluoromethylbenzyl; and $n$ is three.

4. A compound according to claim 3 being the compound 3-[4-(3-diethylaminopropoxy)benzoyl]-2-(4-tolyl)benzofuran.

5. A compound according to claim 3 being the compound 3-[4-(3-diethylaminopropoxy)benzoyl]-2-(4-methoxyphenyl)benzofuran.

6. The compound 2-[4-(3-diethylaminopropoxy)benzoyl]-3-phenylbenzofuran.

7. A compound according to claim 3 being the compound 3-(4-chlorophenyl)-2-[4-(3-diethylaminopropoxy)benzoyl]benzofuran.

8. A compound according to claim 1 being the compound 3-[4-(3-diethylaminopropoxy)benzoyl]-2-phenylbenzothiophene.

9. A compound according to claim 1 being the compound 5-chloro-2-[4-(3-diethylaminopropoxy)benzoyl]-3-phenylbenzothiophene.

10. A compound according to claim 3 being the compound 2-(4-chlorobenzyl)-3-[4-(3-diethylaminopropoxy)-benzoyl]benzofuran.

11. A compound according to claim 3 being the compound 3-[4-(3-diethylaminopropoxy)benzoyl]-2-(4-methoxyphenyl)benzothiophene.

12. The compound 3-[2-(3-diethylaminopropoxy)benzoyl]-2-phenylbenzofuran.

* * * * *

UNITED STATES PATENT AND TRADEMARK OFFICE
CERTIFICATE OF CORRECTION

PATENT NO. : 3,947,470
DATED : March 30, 1976
INVENTOR(S) : L. Martin Brenner, John M. Petta and Stephen T. Ross It is certified that error appears in the above-identified patent and that said Letters Patent are hereby corrected as shown below:

Column 6, line 26, "solt" should read -- soft -- .

Column 7, line 55, " $168^{\circ}$'$170^{\circ}$ " should read -- $168^{\circ}$-$170^{\circ}$ -- .

Column 7, line 64, after "reaction" and before "is" insert -- mixture -- .

Column 10, line 63, after "with" and before "p-" delete "a" .

Column 12, line 37, "Example 2" should read -- Example 1 --.

Column 18, line 57, "2-p-ethoxybenzylbensofuran" should read -- 2-p-ethoxybenzylbenzofuran -- .

Signed and Sealed this

Thirty-first Day of August 1976

[SEAL]

Attest:

RUTH C. MASON
Attesting Officer

C. MARSHALL DANN
Commissioner of Patents and Trademarks